United States Patent [19]

Haris

[11] Patent Number: 4,780,080
[45] Date of Patent: Oct. 25, 1988

[54] ADJUSTABLE DENTOALVEOLAR IMPLANT SYSTEM

[75] Inventor: Andras Haris, Radnor, Pa.

[73] Assignee: Facial Alveodental Implant Rehabilitation Inc., Bala-Cynwyd, Pa.

[21] Appl. No.: 533

[22] Filed: Jan. 5, 1987

[51] Int. Cl.⁴ ............................................. A61C 8/00
[52] U.S. Cl. .................................... 433/173; 433/174
[58] Field of Search ............... 433/174, 175, 176, 173

[56] References Cited

U.S. PATENT DOCUMENTS

| | | | |
|---|---|---|---|
| 4,084,318 | 4/1978 | McEachern | 433/174 |
| 4,531,915 | 7/1985 | Tatum, Jr. | 433/176 |
| 4,552,532 | 11/1985 | Mozsary | 433/174 |
| 4,636,216 | 1/1987 | Tatum | 433/173 |
| 4,657,510 | 4/1987 | Gittleman | 433/174 |

Primary Examiner—John J. Wilson
Attorney, Agent, or Firm—Eugene Chovanes

[57] ABSTRACT

A dental implant system employing a root member which is fixed to the jaw bone. A post is also employed having a first portion fixed to the root and a second portion which extends outwardly from the alveolus of the jaw bone. A head is connected to the post second portion and is angularly disposed in relation to the post. The head is also movable relative to the post to provide various angular orientations for a crown which is fixed to the head.

1 Claim, 1 Drawing Sheet

U.S. Patent  Oct. 25, 1988  4,780,080 ated by reference character 10. The dental implant system 10
ADJUSTABLE DENTOALVEOLAR IMPLANT SYSTEM

BACKGROUND OF THE INVENTION

The present invention relates to a novel dental implant system.

Dental implants have been employed for many years to replace missing teeth or to replace dentures. Generally, the implant includes the use of a titanium screw having a threaded bone and a threaded outer surface. The titanium screw is bonded to the jawbone through osseointergation process, generally believed to take place between the thin layer of titanium oxide on the exterior of the screw and the jawbone. With reference to U.S. Pat. No. 4,552,532, an improvement is shown which includes the provision of a dental implant system which closely mimics the movement of a natural tooth. In that system, the post portion of the implant was generally formed along an axis and placed within the artificial root in a coaxial configuration.

It has been found that successful dental implants must closely match the angle of the existing adjacent teeth found in the jawbone of the patient. In the past, achievement of this result required drilling the jawbone to an angle such that the finished dental implant match the angle of the existing teeth. However, this procedure has proved to be fairly difficult to perform.

A dental implant which solves the problems encountered in the prior art would be a great advance in the dental field.

SUMMARY OF THE INVENTION

In accordance with the present invention a novel and useful dental implant system is provided which permits the dental surgeon to adjust the orientation of crown portion of the dental implant.

The invention employs as one of its elements a root which includes means for fixing the root to the jawbone. The root includes a portion that extends into the alveolus. A post is also provided and includes a first portion and a second portion. Means is included for supporting the first portion of the post to the root. The second portion of the post extends outwardly from the alveolus.

The invention also includes the provision of a head which is connectable to the second portion of the post. The head is angularly disposed in relation to the post and is movable relative to the post. To this end, the head may include a cavity which connects to the second portion of the post such that the head rotates relative to the post. In this case, the post second portion would serve as a pivot and is located within the head cavity.

Means is also found in the present invention for fixing the head to the second portion of the post. The head may be fixed at a selected position relative to the post resulting from the rotational movement of the head relative to the post. Thus, the dental surgeon may form a crown which matches the angle of the adjacent teeth of the patient with the angularly disposed head serving as core for the crown.

It may be apparent that a novel and useful dental implant system has been provided.

It is therefore an object of the present invention to provide a dental implant system which permits the surgeon to form a crown in conjunction with the implant which matches the angular orientation of the adjacent teeth of the patient.

It is another object of the present invention to provide a dental implant system which includes a movable portion which is used as a base support member for a crown which is quickly and easily fixed relative to a post of an implant system.

Another object of the present invention is to provide a dental implant system which possess an asethetically acceptable crown portion of the implant.

Yet another object of the present invention is to provide a dental implant which exhibits versatility such that an aligned crown may be fixed on root portions installed along various axes.

A further object of the present invention is to provide a dental implant system which includes means for preventing the twisting or unscrewing of the root portion of the two-stage dental implant.

The invention possesses other objects and advantages especially as concerns particular characteristics and features thereof which will become apparent as the specification continues.

Figure 3:
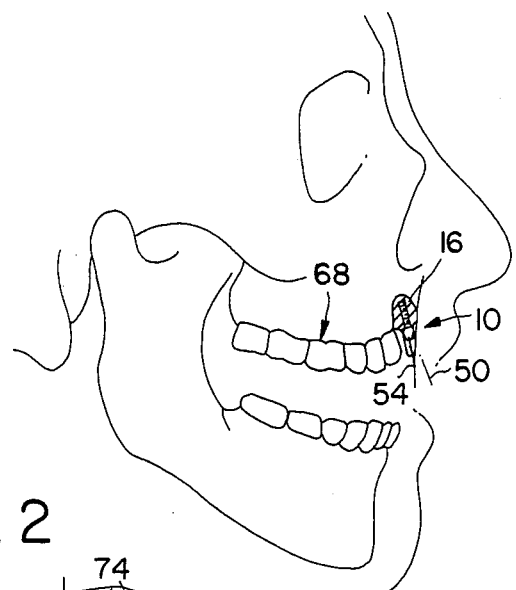
FIG. 3 is a schematic view of the present invention depicting the implant system thereof in section in the jawbone of a human.

For a better understanding of the invention reference is made to the following detailed description of the preferred embodiments hereof which will become apparent as the specification continues.

DESCRIPTION OF THE PREFERRED EMBODIMENTS

Various aspects of the present invention will evolve from the detailed description of the preferred embodiments which should be referenced to the hereinabove drawings.

The invention as a whole is denoted in the drawings by reference character 10. The dental implant system 10 includes as one of its elements a root 12 which may be constructed of titanium or other relatively rigid materials which are non-reactive with human tissue. Root 12 includes an externally threaded portion 14 which bonds to the jawbone 16. Root 12 possesses an interior surface 18 formed with a multiplicity of grooves 20. A resilient member 22 serves as cushion between root 12 and post 24, which threads to the interior surface 26 of resilient member 22. Root 12 is placed in the alveolus 28 which was formerly occupied by a natural tooth, FIG. 1.

Post 24 includes a first portion 30 and a second portion 32. First portion 30 of root 12 includes means 34 for supporting first portion of post 24 to root 12. Means 34 may take the form of a threaded exterior surface 36 of post 24 which threadingly engages threaded interior surface 26 of resilient member 22. Plurality of grooves of root 12 are occupied by protuberances of resilient member 22. Thus, first portion 30 of post 24 is fixed relative to root 12. Second portion 22 of post 24 extends outwardly from alveolus 28 and away from jawbone 16. Gingival layers 40 extend around second portion 32 of post 24. Resilient member 22 may be constructed of Teflon, silicone rubber and the like. Post 24 employs material similar to material used for the construction of root 12.

Second portion 32 of post 24 terminates in a cylindrical tip 42 which includes a slot 44. Slot 44 may be engaged by a screw driver to screw post 24 into place within root 12.

Figure 1:
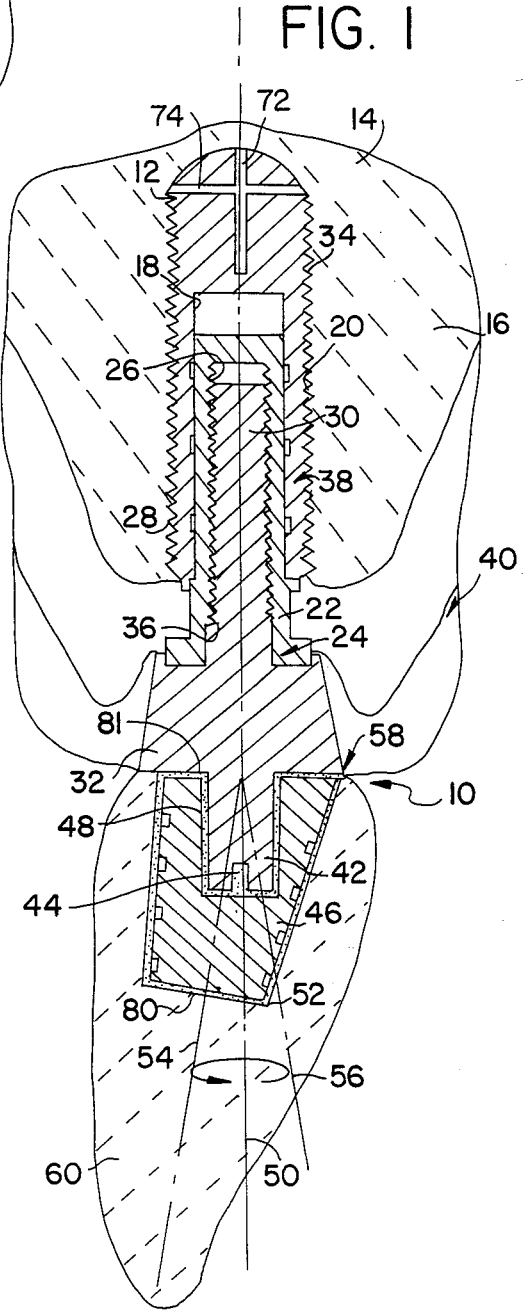
FIG. 1 is a sectional view of the implant system taken along the axis of the implant system root.

The present implant system 12 also possesses a head 46 constructed of titanium or similar material. Head 46 includes a cylindrical cavity 48 which is oriented along axis 50 of root 12 and post 24. Cavity 48 of head 46 circumvents tip 42 of second portion 32 of root 34, tip 42 serving as a pivot for rotation of head 46 relative to post 24. It should be noted, that the exterior surface of head 46 of frusto-conical shape 52 and is angularly disposed relative to axis 50, along which lies root 12 and post 24. As depicted in FIG. 1, exterior surface of frusto-conical shape 52 of head 46 lies along axis 54. Axis 54 is the longitudinal central axis of frusto-conical shape 52. Top surface 80 of head 46 forms a plane perpendicular to the axis 54, while the base 81 of the head is cut such as to form a plane at an angle to the axis 54 of the head 46. Although the angular orientation of axis 54 relative to axis 50 is shown as being approximately 10 degrees, head 46 along axis 54 may be disposed at higher or lower angles e.g: ranging from 5 degrees to 25 degrees. Directional arrow 56 depicts the rotation of head 46 relative to tip 42 of post second portion 32. Means 58 is included for fixing head 46 to cylindrical tip 42. Means 58 may take the form of a quick setting adhesive, commonly identified under the designation "dental cement". Crown 60 is then formed around head 46 after the latter has been fixed to post 24 via means 58.

Figure 2:
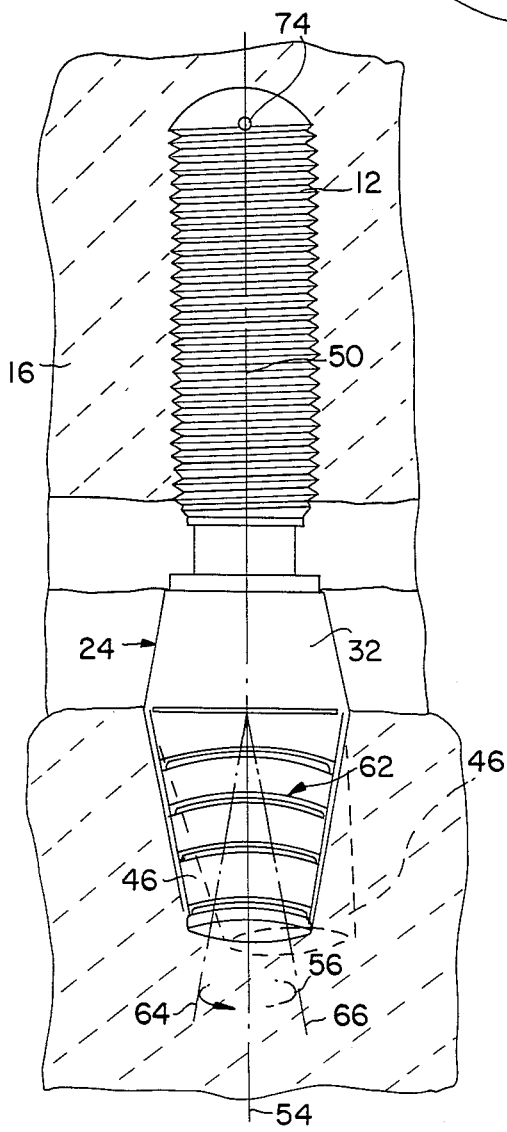
FIG. 2 is a rear elevational view of the implant system of the present invention turned ninety degrees from FIG. 1 showing the crown and human anatomy in section.

With reference to FIG. 2, the implant depicted in FIG. 1 has been turned 90°. Multiplicity of grooves 62 found on the exterior surface 62 of head 46 aid in the holding of crown 60 to head 46. Axes 64 and 66 are also illustrated to represent other possible axes of angular orientation of the exterior surface 52 of head 46, prior to the forming of crown 60. Although head 46 has been described as being compatible with root 12 and post 24, hereinabove shown, head may be employed in any two-stage dental implant.

The implant 10 also includes means 70 for preventing the rotation of root 12. Means 70 takes the form in the present embodiment, of a pair of bores 72 and 74 which penetrate root 12 orthogonally in relation to one another. Bores 72 and 74 permit the entry and growth of bone cells, therewithin. Such bone cell growth serves as an anchor which resists turning forces on root 12.

In operation, the implant 10 is placed relative to the existing dental structure 68 of a patient depicted in FIG. 3. After implantation of the root 12, resilient member 22, and post 24 along axis 50 head 46 is placed over tip 42 of post 24. Head 46 is rotated relative to axis 50, to provide the desired angular orientation of the exterior surface 62 of head 46 relative to axis 50, FIGS. 1 and 2. As depicted in FIGS. 1-3, head 46 has been oriented to lie along axis 54. Thus, crown 50 is formed with a slight inward angle relative to root 12 which lies along axis 50. Of course, crown 60 would be oriented to match the existing dental structure 68 i.e. Crown 60 would lie substantially parallel to adjacent teeth in dental structure 68. Rotation of head 46 90° in either direction about axis 60 would permit the surgeon to form a crown which appears essentially coincident with axis 50 in the two dimensional representation of FIG. 1. With reference to FIG. 2, a phantom depiction 46A of head 46 in this position is shown along axis 66. Although head 46A appears angular from the front or rear thereof, this cant or tilt will disappear when crown 60 is formed around head 46A along axis 50. Of course, crown 60 may be formed at various angles by rotation of head 46 as shown by directional arrow 56. The implant 10 also permits alignment of crown 60 with the adjacent dental structure 68 where root 12 is not placed exactly along axis 50. Means 70 prevents the rotation or unscrewing of root 12 when the remaining components of implant 10 are being placed in jawbone 16, and during the time subsequent to implantation.

While in the foregoing embodiments of the present invention have been set forth in considerable detail for the purposes of making a complete disclosure of the invention, it may be apparent to those of skill in the art that numerous changes may be made in detail without departing from the spirit and principles of the invention.

What is claimed is:

1. A dental implant system intended for placement in an alveolus of the jawbone and for use with a crown, comprising in combination:
    (a) a root having means for fixing the root to the jawbone and a portion extending into the alveolus;
    (b) a post with
        (1) a first portion fixed in the root and
        (2) a second portion having
            (a) a post base having a circular cross section adjacent the root and
            (b) a cylindrical tip
                (1) with a cross section smaller than the post base cross section,
            (c) extending from the post base, and
            (c) a shoulder extending transversely of the second portion between the post base and tip;
    the tip extending into
        (c) a head having
            (1) a cylindrical cavity receiving the tip in close fit,
            (2) a head base extending transversely of the cylindrical cavity, and
            (3) a frusto-conical shape having a longitudinal central axis and having a surface opposite the head base in a plane normal to the longitudinal central axis of the head, and
    said head base having a surface in a plane at an angle to the longitudinal central axis of said head;
    the root, the post including its base and tip, and the head cavity lying along a common longitudinal axis; the head base resting against the post shoulder;
    (d) adhesive means fixing the head on the post at a selective rotational position, and
    (e) a crown on the head,
    whereby
    when said head base rests against said shoulder, the longitudinal central axis of said head forms an angle with said common longitudinal axis of said root, the post including its base and tip, and the head cavity.

* * * * *